United States Patent [19]

Drennen, III

[11] Patent Number: 5,214,277
[45] Date of Patent: May 25, 1993

[54] NEAR-INFRARED REFLECTANCE SPECTROMETER SYSTEM AND RELATED SAMPLE CELL AND SAMPLE SUPPORT

[76] Inventor: James K. Drennen, III, One Old North Church St., Natrona Heights, Pa. 15065

[21] Appl. No.: 898,454

[22] Filed: Jun. 15, 1992

[51] Int. Cl.[5] .................. H01J 3/14; G01N 21/01
[52] U.S. Cl. ........................ 250/216; 356/244; 250/576
[58] Field of Search ............ 356/244, 237; 250/216, 250/222.1, 222.2, 576, 239, 339, 353; 209/576, 577, 587, 588, 912

[56] References Cited

U.S. PATENT DOCUMENTS

| | | |
|---|---|---|
| 3,947,121 | 3/1976 | Cotter et al. .................. 356/244 |
| 3,999,866 | 12/1976 | Mathisen ........................ 356/244 |
| 4,303,339 | 12/1981 | Gläser et al. ................... 356/244 |
| 4,847,487 | 7/1989 | Bordini ........................ 250/223 R |
| 4,882,493 | 1/1989 | Lodder et al. . | |
| 4,893,253 | 1/1990 | Lodder . | |
| 5,015,092 | 5/1991 | Sting ............................ 356/244 |
| 5,017,341 | 5/1991 | Takekawa ...................... 356/244 |

FOREIGN PATENT DOCUMENTS 8607288 12/1986 PCT Int'l Appl. ................ 356/244

Primary Examiner—David C. Nelms
Assistant Examiner—Michael Messinger
Attorney, Agent, or Firm—Arnold B. Silverman; Suzanne Kikel

[57] ABSTRACT

The present invention relates to a cell or holder or reflector for NIRS samples, such as capsules, tablets, or liquids. The cell comprises a main body with a top surface defining a recess. The recess is generally axially symmetrical and diverges generally upwardly from the bottom to the top of the recess. A central 90° conical projection is located at the bottom of the recess and forms an annular groove with the sidewall of the recess. The sidewall of the recess has an annular notch for receiving and supporting a support window. This sidewall of the recess is parabolically shaped from the bottom to the top of the recess. The support window has intersecting grooves in its top surface over which the sample rests, or in which the sample is supported.

32 Claims, 3 Drawing Sheets

NEAR-INFRARED REFLECTANCE SPECTROMETER SYSTEM AND RELATED SAMPLE CELL AND SAMPLE SUPPORT

BACKGROUND OF THE INVENTION

1. Field of the Invention

The present invention relates to a sample holder or cell or reflector for use in near-infrared reflectance spectrometers, which is an instrument used to identify the components and/or concentrations of components in a product.

2. Description of the Prior Art

Near-infrared reflectance spectroscopy or spectrometer (NIRS) which originated as a method or means for analysis of agricultural products is now being used for analysis of pharmaceuticals.

For such pharmaceutical analysis, which involves analyses of certain intact solid samples, such as capsules or tablets, a sample holder has been designed. Such a sample holder for a tablet or capsule is disclosed in U.S. Pat. No. 4,882,493 issuing on Nov. 21, 1989, to Robert A. Lodder et al., which is incorporated herein by reference along with the copending application Ser. No. 07/166,211 filed on Mar. 10, 1988.

The sample holder of U.S. Pat. No. 4,882,493 illustrates a receptacle with a conical shaped surface which reflects radiation from the sample, which is substantially diffuse reflectance, back to a detector. The bulk of the radiation which reaches the detector of a NIRS instrument is radiation that is scattered or diffusely reflected by the contents of either the capsule or the tablet. Even though the conical configuration of the receptacle reduces undesired specular reflectance, the sensitivity level of the NIRS instrument using the conical receptacle of U.S. Pat. No. 4,882,493 or using any other form of the prior art may be improved A higher degree of sensitivity of the NIRS instrument is becoming increasingly important when measuring lower concentrations and/or smaller amounts of a sample relating to various scientific fields. For instance, pharmaceutical scientists need to analyze low level degradant products in solid state form while the capsule or tablet is still intact. Similar instrument sensitivity demands exist also for the agricultural scientist in analyzing whole grain kernels, or for the polymer scientist in analyzing polymer pellets where the kernels and pellets are of substantially lower concentrations and/or smaller amounts than were previously measured.

Additionally, the prior art uses different sample cells when measuring a capsule, or a tablet, or a liquid sample. That is, one sample holder is used for analysis of a tablet or liquid, and another type of holder is used for analyzing capsules.

Furthermore, the sample cell of the prior art analyzes capsules in a vertical position. The lower segments of the capsule receives up to 39 times less illumination than the top segments. Also, the bottom end of the capsule is either not illuminated or is barely illuminated in view of its being hidden in the bottom of the receptacle.

In spite of the known sample holder devices that are presently used in near-infrared reflectance spectrometers for analyzing agricultural, pharmaceutical, and other products, there remains a very real and substantial need for a sample cell that would improve sensitivity and thereby give more accurate analysis of such products. There is also a need for one or a universal sample cell which can be used for analysis of either a liquid, a capsule, or a tablet.

SUMMARY OF THE INVENTION

The present invention has met the above-described needs. A sample cell of the present invention provides for a more sensitive NIRS instrument and, therefore, a more accurate analysis of the product, and also a construction for a sample cell which can be interchangeably used either for a capsule, a tablet, or a liquid.

The sample cell of the invention preferably provides a main body having a top surface with a recess. This recess is generally axially symmetrical, and diverges generally upwardly to the top surface. An inner 90° cone is centrally located in the bottom of this recess, and has a vertex extending upwardly in the recess. This inner 90° cone is smaller than the diameter of the recess and has a conical surface which forms an annular groove at the bottom of the recess with the wall of the recess. The wall or side surface of the recess is substantially parabolic when considered from the bottom of the recess upwardly to the top surface of the sample cell. Midway along the wall of the recess may be an annular notch or a cutout area for receiving and supporting a supporting window which carries or supports the sample.

Preferably, the support window is a circular plate made from quartz, glass, sapphire or diamond and will fit into the annular notch of the recess if a notch is provided or will be wedged against the wall of the recess if no annular notch is provided. This circular plate has two intersecting machined grooves in its top surface for positioning a capsule or a tablet which lays over the machined grooves, or for containing a liquid.

Accordingly, it is an object of the present invention to provide a sample cell or reflector for small samples for analysis using NIRS which enhances the sensitivity of the results obtainable by the instrumentation.

A further object of the present invention is to provide a design for a sample cell or reflector for small samples for analysis using NIRS which allows the same sample cell or holder to be interchangeably used for analysis of an individual intact capsule or tablet, a liquid, or other samples.

It is a further object of the invention to provide a sample cell for samples using NIRS which has surfaces which direct light onto the sample, which collect light that is diffusely reflected from the sample, and which direct the light back towards the detectors in a more efficient manner than previous cell designs.

It is a further object of the present invention to provide an improved sample cell or reflector for samples using NIRS which decrease the noise and therefore increases the signal-to-noise ratio resulting in a more sensitive instrumental system.

A still further object of the present invention is to provide a sample cell or reflector for NIRS analysis which can be used in a wide variety of fields, such as pharmaceuticals, agriculture, or polymer chemistry.

It is a further object of the present invention to provide an improved sample cell or reflector for analysis using NIRS which directs the incident light towards a sample in a more effective manner than previously.

It is a still further object of the present invention to provide a sample cell or reflector for using NIRS analysis which has a recess with a substantially parabolic shaped surface.

A further object of the present invention is to provide a sample cell or reflector for NIRS analysis which is constructed and designed such that the same sample cell or reflector can be used to support any type of sample without changing the holder or any components of the holder in order to enable analysis of the sample.

A still further object of the present invention is to provide a sample holder for using NIRS analysis whereby substantially all of the surfaces of every type of sample are illuminated It is still a further object of the present invention to provide a sample cell or reflector for using NIRS analysis wherein the analysis of every type of sample the variation in illumination from the top to the bottom of the sample is reduced significantly, resulting in a more consistent illumination of all surfaces.

A broader object of the present invention is to provide an improved NIRS system with an increase in sensitivity, and which can be used for analyzing a wide variety of products.

These and other objects of the present invention will be more fully understood and appreciated from the following description of the invention, on reference to the illustrations appended thereto.

DETAILED DESCRIPTION OF THE PREFERRED EMBODIMENT

It is to be understood that the term "spectrometer" as used herein is defined as being a spectrochemical instrument which employs a monochromator in conjunction with photoelectric detection of isolated wavelength bands to resolve, collect, and display a spectrum of luminous radiation.

A near-infrared diffuse reflectance spectrometer is a spectrometer that measures primarily radiation in the near infrared segment of the electromagnetic spectrum that is diffusely reflected from a sample. The instrument and computer controls can then display a reflectance or absorbance spectrum of the sample from which the scientist obtains chemical and physical information about the sample. The following expression is well-known in the art and applies to the NIRS system:

$$\log \frac{1}{\text{reflectance}} \simeq \text{absorbance}$$

In an NIRS system, the reflected radiation is either specular reflectance or diffuse reflectance. Specular reflectance is light reflected from the surface of the sample and/or cell holder which contains no information about the chemical nature of the sample. Diffuse reflection NIR spectroscopy involves diffusely reflected light which is light that penetrates the sample, interacts with the molecules, and then reflects in a diffuse manner. The invention performs diffuse reflectance NIR spectroscopy. The invention is used as a device to contain and support pharmaceutical and other samples, and to present these samples to the near-infrared reflectance spectrometer. The present invention may be used with numerous spectrometers from various manufacturers.

Figure 1:
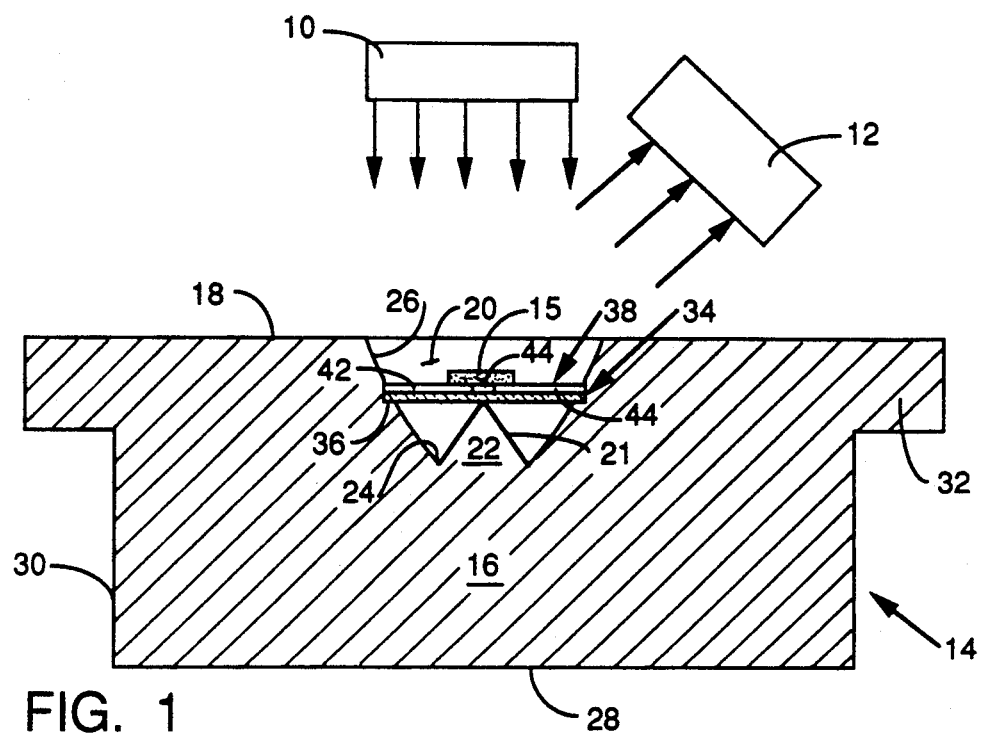
FIG. 1 is a partial schematic view of an NIRS system including a sample cell of the present invention in cross section.

FIG. 1 illustrates a near-infrared reflectance spectrometer (NIRS) system comprising a light source 10, a detector 12 and a sample cell 14, with a sample 15. Only one detector 12 is shown, but it is to be understood that an NIRS system has several detectors at various locations and angles within the instrument.

Figure 2:
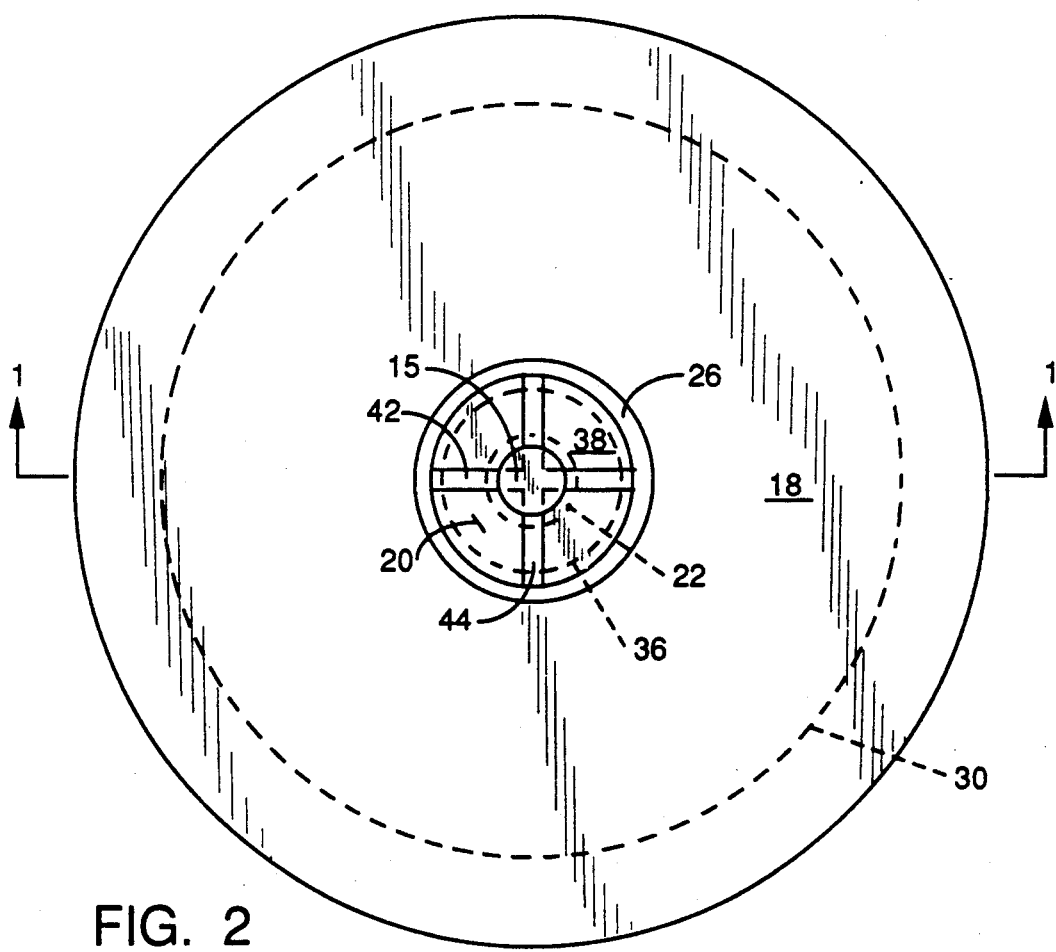
FIG. 2 is a top plan view of the sample cell of the present invention of FIG. 1.
Figure 3:
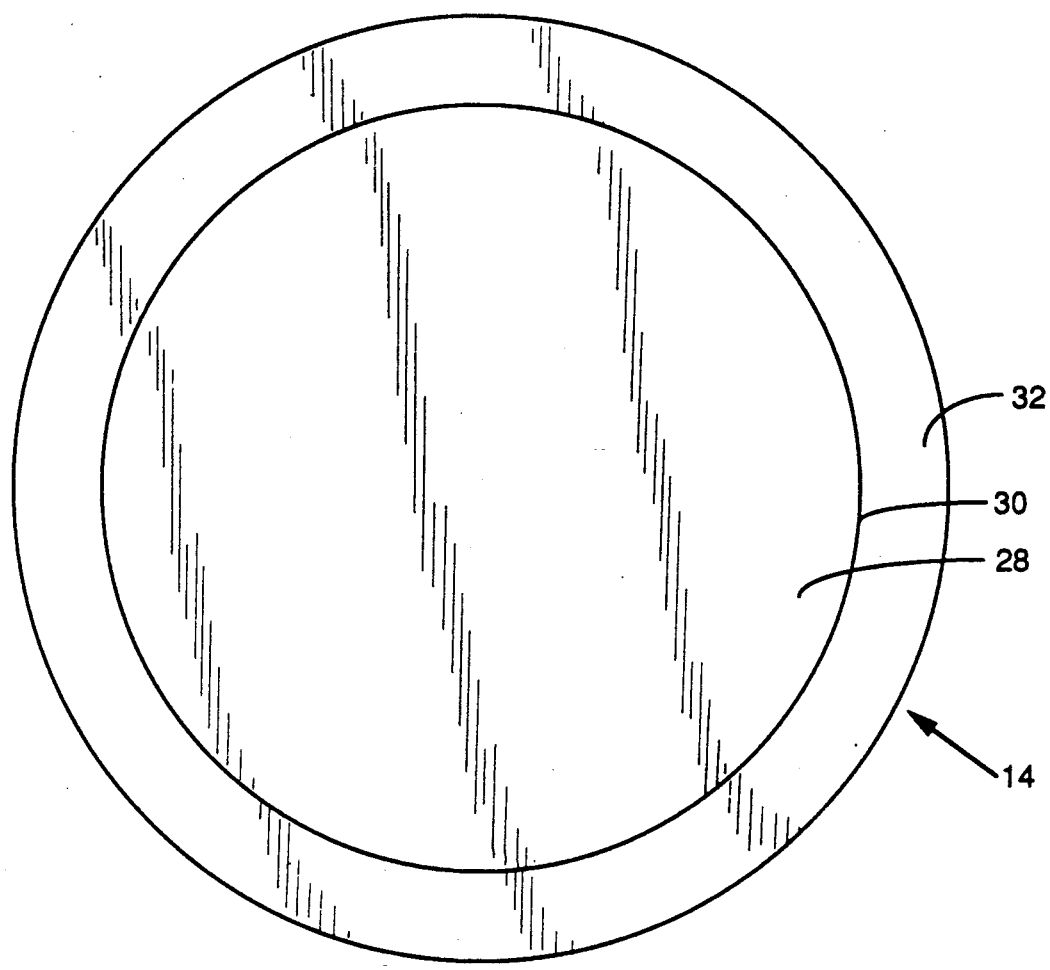
FIG. 3 is a bottom plan view of the sample cell of FIG. 1.

The sample cell 14 comprises main body 16, having a top surface 18 defining a recess 20. Recess 20 is generally axially symmetrical and diverges generally upwardly to top surface 18. In recess 20 is an inner 90° cone-shaped protrusion 22 having a vertex which projects outwardly in recess 20. Cone 22 is smaller in diameter and height than recess 20 and has a surface 21 which is machined. As shown in FIGS. 1 and 2, inner cone 22 in recess 20 forms an annular groove 24 at the bottom of recess 20 with a sidewall or surface 26 of recess 20. Preferably, annular groove 24 is circular. Preferably, both the recess 20 and cone 22 are an integral part of and are formed in main body 16 by a diamond machining process.

Preferably, main body 16, as well as sidewall 26 of recess 20, and wall 21 of cone 22, are constructed from a material which is reflective in the near-infrared region of the spectrum. Preferably, this material is aluminum referred to as 60/61-T6. Main body 16, sidewall 26, and wall 21 may be made of gold or may be plated with aluminum or gold. Reflective coatings will generally be between 2000 to 5000 Angstroms thick. Main body 16 is circular and of a size and shape which fits into a solid-sample drawer of a near-infrared reflectance spectrometer, such as a Bran+Luebbe InfraAlyzer 400 or InfraAlyzer 500 Spectrometer. In addition, the dimension of main body 16 must comport with the diameter of the incident beam of light source 10 of the near-infrared reflectance spectrometer system of FIG. 1. The diameter of the incident beam will vary from one instrument to another, and even for one instrument depending on the particular optical configuration. The diameter of the incident beam is the diameter of the beam of the light emerging from the near-infrared reflectance (NIR) instrument to strike the sample.

Main body 16 has a lower portion with a bottom surface 28 and a sidewall 30, and an upper flange portion indicated at 32. Preferably, the diameter of the lower portion of main body 16 with bottom surface 28 and sidewall 30 is about 2.98 inches, but this dimension can range from about 1.40 to about 5.00 inches. Preferably, the diameter of upper flange portion 32 of main body 16 is about 3.25 inches, but this dimension can range from about 1.40 to about 5.00 inches. Preferably, the thickness of flange portion 32 is about 0.33 inches, but this dimension can range from about 0.10 to about 0.50 inches. Preferably, the total height of sample holder 14 is about 1.5 inches, but this dimension can range from about 1.13 to about 3.0 inches. Preferably, the flange portion 32 extends away from sidewall 30 about 0.27 inches, but this dimension can range from about 0.10 to about 2.60 inches.

Still referring to FIG. 1, the sidewall 26 of recess 20 forms a substantially parabolic shape when considered from annular groove 24 at the bottom of inner cone 22 upwardly to the top surface 18 of the flange portion 32 of main body 16, more about which will be discussed hereinafter. At or near the mid-point along inner annular sidewall 26 of recess 20 is an annular notch or grooved area 34 which circles around annular wall 26 of recess 20, and which forms a ledge 36 for supporting a support window 38 which, in turn, supports sample 15. Even though FIG. 1 shows a grooved area 34 for supporting the support window 38, no such grooved area 34 may be provided along sidewall 26 of recess 20, in which case, support window 38 would be supported by sidewall 26.

Preferably, the height of cone 22 is about 0.38 inches and can be in the range from about 0.125 to about 1.2 inches. The diameter of cone 22 at its base near annular groove 24 is preferably about 0.38 inches, and can range from about 0.125 to about 0.50 inches. The distance from top surface 18 of cell 14 down to annular notch 34 in sidewall 26 of recess 20 is preferably about 0.241 inches, and can range from about 0.0625 inches to about 0.5 inches. The depth of recess 20 from top surface 18 to annular groove 24 is preferably about 0.50 inches and can be in the range from about 0.125 inches to about 1.50 inches. The diameter of recess 20 at its top surface 18 is preferably about 1.20 inches, and can be in the range from about 0.50 inches to about 2.0 inches. Preferably, the center of recess 20 aligns with the center of main body of sample cell 14. As can be particularly seen in FIG. 1, annular notch 34 supports the support window 38 in recess 20.

Preferably, the height of cone 22 is about 80% of the depth of recess 20. This percentage may range from about 20% to about 100%.

FIGS. 1 and 2 show different views of the manner in which support window 38 supports sample 15.

Figure 4:
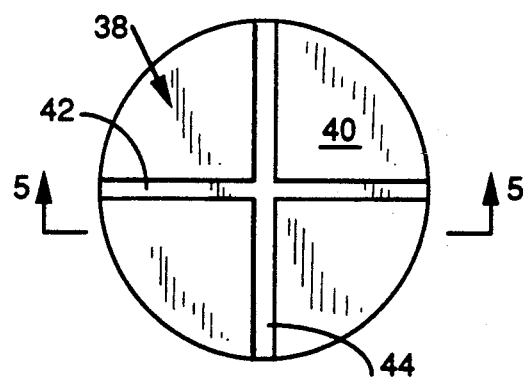
FIG. 4 is a top plan view of a support window for supporting a product, and used in the sample cell of FIG. 1.
Figure 5:
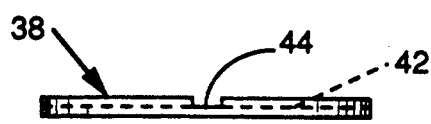
FIG. 5 is a side elevational view taken along lines 5—5 of FIG. 4.

FIGS. 4 and 5 better illustrate support window 38. Referring particularly to FIG. 4, support window 38 is preferably a circular disc or plate, which preferably is about 2 millimeters in thickness and about 20 mm in diameter. The top surface 40 of support window 38 has two longitudinal grooves 42 and 44 which intersect at or near the center of window 38. Grooves 42 and 44 are preferably machined, and are about 2.5 mm wide and about 0.5 mm deep. Preferably, window 38 is made of a material which is transparent or translucent in the near-infrared region of the electromagnetic spectrum. Window 38 is preferably made of a sapphire or a quartz, but can be made of any other kind of glass or diamond, fits directly into annular notch 34, and is supported on ledge 36 in notch 34 of recess 20 of cell 14. Preferably, the surfaces of window 38 including those of grooves 42 and 44 are polished and coated with an anti-reflective material, such as silicone dioxide, titanium dioxide, a combination of the two, or other materials. The thickness of the anti-reflective coating may be about 2500 Angstroms. The polishing of both the reflective aluminum or gold reflective recess 20 can be done with a lapping compound.

Grooves 42 and 44 in the top surface 40 of window 38 allow consistent placement of sample 15. Preferably, if sample 15 is a capsule, it is disposed in the intersection of grooves 42 and 44 in an upright position, or if the size of the capsule is smaller, it can be positioned in any section of groove 42 or 44 on its side. No additional means are necessary to secure the capsule in its desired position other than grooves 42 and 44.

In FIG. 1, sample 15 is shown to be a tablet. When testing a tablet, preferably, it is disposed directly over the intersection of grooves 42 and 44, or such a tablet may be disposed over any other section of the grooves.

The positioning of the sample 15 on support window 38 is very important, whether the sample be a capsule, tablet or a liquid or any other kind of product. Grooves 42 and 44 are used to assist in obtaining a consistent sample placement of the sample and to prevent the sample from rolling or sliding on support window 38 as the sample cell 14 is positioned for analysis, i.e. when the sample drawer is closed. The sample is most uniformly illuminated on all surfaces if it is placed in the center of the window, i.e. at the intersection of grooves 42 and 44, and in the center of the light beam from source 10. A consistent sample placement or positioning is extremely important in regulating spectral reflectance and in obtaining reproducible sample spectra. The sample support window 38 with grooves 42 and 44 gives more consistent sample positioning than the support wires of the prior art.

In testing a sample, whether it is a capsule, tablet, or liquid, the sample is supported by window 38 and window 38 is either already disposed in recess 20 or is positioned in annular notch 34 of recess 20, and source light 10 shown in FIG. 1 is actuated to direct its beam onto the sample, in a manner well-known in the art. Detector 12 detects the reflected and/or refracted light being emitted from surface 26 of recess 20, surface 40 of window 38, the surfaces of grooves 42 and 44 of window 38, surface 21 of cone 22 and the surfaces of sample 15.

Grooves 42 and 44 are shown in support window 38, however, it is to be understood that there may be no grooves in window 38 without distracting from the gist or spirit of the present invention.

Figure 6:
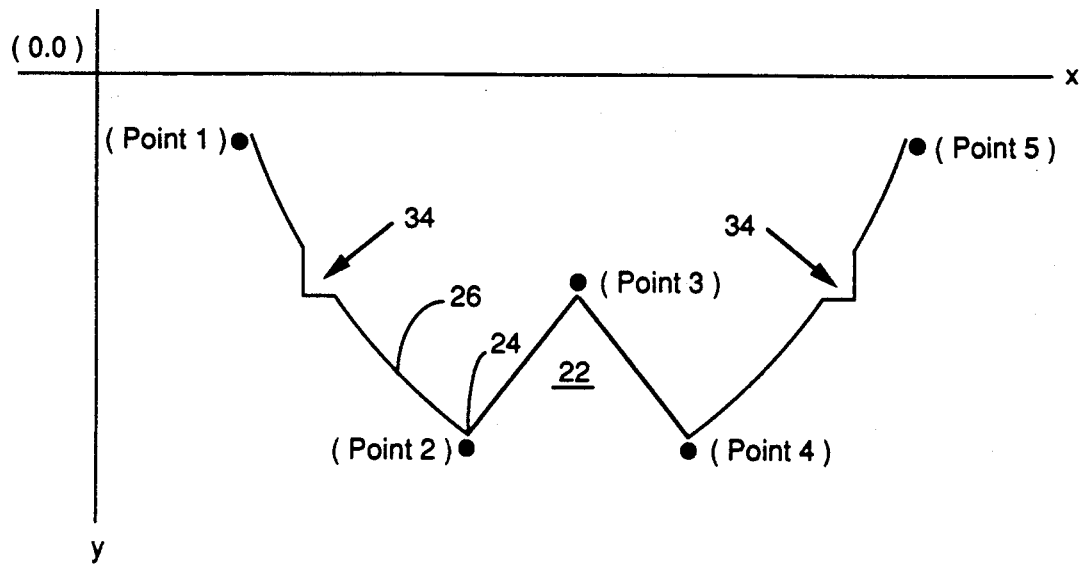
FIG. 6 is a schematic showing in exaggerated form the parabolic surfaces of the recess of FIG. 1, and illustrates an annular notch for supporting the support window of FIG. 4.
Figure 7A:
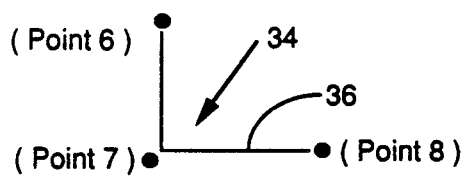
FIGS. 7A and 7B are enlarged, schematic views of the annular notch shown in FIG. 6.
Figure 7B:
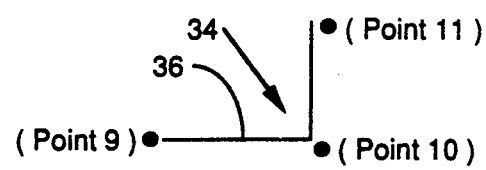

FIG. 6 better illustrates the parabolic shape of surface 26 of recess 20, and FIGS. 7A and 7B better illustrate annular notch 34 in surface 26 of recess 20.

Referring to the graph of FIG. 6, the parabolic surface 26 of inner receptacle or recess 20 of sample cell 14 is defined by several dots which represent specific points (x, y) on the parabola along the x and y axes. The first dot starting at the far left of FIG. 6 is 4.0842 and $-8.7476$, and is indicated as point 1; the second dot is 4.4959 and $-9.1782$ and is indicated as point 2; the third dot is 4.6842 and $-8.9882$ and is indicated as point 3; the fourth dot is 4.8759 and $-9.1782$ and is indicated as point 4; and the fifth dot is 5.2842 and $-8.7476$, and is indicated as point 5.

The annular notch 34 also has several dots indicated in FIGS. 7A and 7B, which also represent specific points (x, y) along the x and y axes of FIG. 6. Referring to FIG. 7A, the vertical length of notch 34 ranges from 4.2826 and $-8.9576$ which is point 6 to 4.2826 and $-8.9782$ which is point 7, and the horizontal length of ledge 36 is from 4.2826 and $-8.9782$ (point 7) to 4.3023 and $-8.9782$, which is point 8. Referring to FIG. 7B, the horizontal length of ledge 34 ranges from 5.0661 and $-8.9782$ which is point 9 to 5.0858 and $-8.9782$, which is point 10. The vertical height of notch 34 ranges from 5.0858 and $-8.9782$ (point 10) to 5.0858 and $-8.9576$, which is point 11. The distance between points 8 and 9 is about 0.7638 inches, and the distance between points 7 and 10 is about 0.8032 inches.

In that these several dots or points define the parabola for the inner surface 26 of recess 20 and the notch 34, the corresponding x and y values for these points 1–11 are used by a machinist to set up a computerized lathe or mill. These points 1–11 are in units of inches for the x and y values.

The following equation preferably is employed to obtain the y value for the parabolic curve of the reflective surface 26 of recess 20 in cell 14:

$$y = \frac{136.88 \sqrt{x}}{31.623}$$

where x is the component along the x-axis for the several points 1–6, 8, 9, and 11 for the parabolic surface 26.

Preferably, ledge 36 is about 0.04 inches wide, and the depth of annular notch 34 is about 0.03 inches. The former dimension may range from about 0.03 inches to about 0.01 inches. The latter dimension may range from about 0.02 inches to about 0.01 inches. Preferably, the inner ends of ledge 36 are about 0.7638 inches apart and this distance may range from about 0.125 inches to about 0.50 inches. The outer ends of ledge 36 are about 0.8032 inches apart, and this distance may range from about 0.135 inches to about 0.60 inches.

It is well known in the art that an NIRS instrument uses collimating lenses to direct collimated light onto a sample. However, it is also generally known that light when it reaches a sample is not truly collimated. The parabolic shape of reflective surface 26 of recess 20 of sample cell 14 helps to focus the reflected light from source 10 onto the sides and bottom of sample 15 more effectively. This parabolic shape of sidewall 26 of cell 14 directs the light onto the sides and bottom of sample 15; collects the diffused, reflected light from the bottom and sides of sample 15; and directs the diffusely reflected light back to the detectors of the NIRS system in a more efficient and effective manner than prior art sample cells.

The result is an increase in the electrical signal-to-noise ratio (S/N) in that there is a decrease in noise compared to previous sample holder designs, which, in turn, results in a more sensitive instrumental system.

The sample holder design of the present invention was tested against the prior art of the type disclosed in U.S. Pat. No. 4,882,493 to compare the noise levels of each. The test for both sample cells was carried out in a Bran+Luebbe InfraAlyzer 500 Near-Infrared Spectrometer in a diffuse reflectance mode. This spectrometer is similar to that schematically illustrated in FIG. 1. The noise level for the conical surface cell of the prior art was 22 microabsorbance units when referenced to zero. The noise level for the parabolic surface of the sample cell holder of the invention was 15 microabsorbance units when referenced to zero This represents a 32% improvement in the reduction in noise for the sample cell of the present invention.

The parabolic surface 26 of sample holder 14 as illustrated in FIGS. 6, 7A and 7B and discussed hereinbefore was used in the tests performed by the InfraAlyzer 500 Near-Infrared Spectrometer. The dimensions, including the specific points 1–11, and the parabolic equation of the optical parabolic surface of the sample holders which are built for other brands of instruments, may vary, however, depending upon the optical design of the instrument. Also, these features of the parabolic surface 26 may be modified to accommodate different sizes of the sample being analyzed However, the range of dimensions including the specific points that have been discussed herein should accommodate most pharmaceutical samples. An optimum parabola for efficient analysis of a sample in a particular instrument can be calculated when the distance from the source to the sample and the width of the incident beam are known.

In the sample cell of the present invention, preferably capsules are analyzed in a horizontal position. In view of this, the capsule receives more consistent illumination on all its surfaces compared to the sample cell of the prior art where the capsule is analyzed in a vertical position.

From the foregoing, it will be appreciated that the invention provides an improved NIRS system, an improved sample holder, and an improved support for the sample used in an NIRS system.

While the foregoing has been described with respect to the preferred embodiment and alternatives thereto, they are not intended nor should they be construed as limitations on the invention, as one skilled in the art would understand many variations and modifications of this embodiment may be made which fall within the spirit and scope of this invention.

In accordance with the provisions of the patent statutes, I have explained the principles and operation of my invention and have illustrated and described what I consider to represent the best embodiment thereof.

I claim:

1. An apparatus for a near-infrared reflectance spectrometer used for analyzing a sample, comprising:
   light source means for supplying light to said sample, which light reflects off of said sample,
   sample cell means for supporting said sample,
   detector means for receiving said reflected light from said sample,
   said sample cell means, comprising:
   a main body having a top surface defining a recess with a bottom and a sidewall,
   support means in said recess for said supporting of said sample,
   said sidewall of said recess being substantially parabolically shaped from said bottom of said recess to said top surface of said main body of said sample cell means.

2. An apparatus of claim 1, wherein said recess is centrally located relative to said top surface of said main body.

3. An apparatus of claim 1, wherein said support means is a support window means and made of a transparent or a translucent material in the near-infrared region of the electromagnetic spectrum.

4. An apparatus of claim 1, wherein said support means is substantially circular plate means including positioning means associated with a top surface of said plate means for positioning said sample.

5. An apparatus of claim 4, wherein said positioning means of said support means are longitudinal grooves in said top surface of said plate means which are centered and which intersect to form a cross in top plan 6. An apparatus of claim 4, wherein said support means has positioning means for supporting a capsule sample.

7. An apparatus of claim 4, wherein said support means has positioning means for supporting a tablet sample.

8. An apparatus of claim 4, wherein said support means has positioning means for supporting a liquid sample.

9. An apparatus of claim 1, wherein said sidewall of said recess is parabolically shaped from said bottom of said recess to said top surface of said main body.

10. An apparatus of claim 1, further comprising:
means in said recess for receiving and supporting said support means.

11. An apparatus of claim 10, wherein said means in said recess for receiving and supporting said support means includes annular notch means in said sidewall of said recess, located generally midway along said sidewall of said recess.

12. An apparatus of claim 11, wherein said annular notch means has a ledge for said supporting of said support means.

13. An apparatus of claim 1, wherein said recess is generally axially symmetrical and diverges generally upwardly from said bottom of said recess to said top surface of said main body of said sample cell.

14. An apparatus of claim 1, further comprising:
an inner cone-shaped projection location in said bottom of said recess and forming a substantially 90° cone portion oriented upwardly out of said recess toward said top surface of said main body, and
said inner projection forming annular groove means with said sidewall of said recess at said bottom of said recess.

15. A sample cell for use in an infrared spectrometer for analyzing a sample, comprising:
a main body having a top surface defining a recess with a bottom and a sidewall, and
support means in said recess for supporting said sample,
said sidewall of said recess being substantially parabolically shaped from said bottom of said recess to said top surface of said main body of said sample cell.

16. A sample cell of claim 15, wherein said recess is centrally located relative to said top surface of said main body.

17. A sample cell of claim 15, wherein said support means is support window means made of a transparent or translucent material in the near-infrared electromagnetic spectrum.

18. A sample cell of claim 15, wherein said support means is substantially circular plate means including positioning means associated with a top surface of said plate means for positioning said sample.

19. A sample cell of claim 18, wherein said positioning means of said support means are longitudinal grooves in said top surface of said plate means, said grooves being centered and which intersect to form a cross in top plan view.

20. A sample cell of claim 18, wherein said support means has positioning means for supporting a capsule sample.

21. A sample cell of claim 18, wherein said support means has positioning means for supporting a table sample.

22. A sample cell of claim 18, wherein said support means has positioning means for supporting a liquid sample.

23. A sample cell of claim 15, wherein said sidewall of said recess is parabolically shaped from said bottom of said recess to said top surface of said main body.

24. A sample cell of claim 15, further comprising:
means in said recess for receiving and supporting said support means.

25. A sample cell of claim 24, wherein said means in said recess for supporting said support means includes annular notch means in said sidewall of said recess located generally midway along said sidewall of said recess.

26. A sample cell of claim 25, wherein said annular notch means has a ledge for said supporting of said support means.

27. A sample cell of claim 15, wherein said recess is generally axially symmetrical and diverges generally upwardly from said bottom of said recess to said top surface of said main body of said sample cell.

28. A sample cell of claim 15, further comprising:
an inner cone-shaped projection located in said bottom of said recess and forming a substantially 90° cone portion oriented upwardly out of said recess toward said top surface of said main body, and
said inner projection forming annular groove means with said sidewall of said recess at said bottom of said recess.

29. A sample cell of claim 15 including: spectrometer for analyzing a sample, comprising:
positioning means associated with a top surface of said support means for positioning said sample on said support means.

30. A sample cell of claim 29, wherein said support means is support window means made of a transparent or translucent material in the near-infrared electromagnetic spectrum.

31. A sample cell of claim 29, wherein said support means is substantially circular plate means.

32. A sample cell of claim 29, wherein said positioning means are longitudinal grooves in said top surface of said support means, said grooves being centered and which intersect to form a cross in top plan view.

* * * * *

UNITED STATES PATENT AND TRADEMARK OFFICE
CERTIFICATE OF CORRECTION

PATENT NO. : 5,214,277
DATED : May 25, 1993
INVENTOR(S) : James K. Drennen, III

It is certified that error appears in the above-indentified patent and that said Letters Patent is hereby corrected as shown below:

Claim 5, column 8, line 62 - after "plan", -- view.-- should be inserted.

Claim 29, column 10, lines 38 and 39 - "spectrometer for analyzing a sample, comprising:" should be deleted.

Signed and Sealed this

Twenty-first Day of February, 1995

Attest:

BRUCE LEHMAN

*Attesting Officer*     *Commissioner of Patents and Trademarks*